United States Patent
Diwinsky et al.

(10) Patent No.: US 9,458,735 B1
(45) Date of Patent: Oct. 4, 2016

(54) SYSTEM AND METHOD FOR PERFORMING A VISUAL INSPECTION OF A GAS TURBINE ENGINE

(71) Applicant: General Electric Company, Schenectady, NY (US)

(72) Inventors: David Scott Diwinsky, West Chester, OH (US); Ser Nam Lim, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/040,310

(22) Filed: Feb. 10, 2016

Related U.S. Application Data

(63) Continuation of application No. 14/963,665, filed on Dec. 9, 2015.

(51) Int. Cl.

| | | |
|---|---|---|
| H04N 7/18 | (2006.01) | |
| F01D 21/00 | (2006.01) | |
| F01D 25/24 | (2006.01) | |
| G01N 21/88 | (2006.01) | |
| G01M 15/14 | (2006.01) | |
| G06T 7/00 | (2006.01) | |
| F02C 7/00 | (2006.01) | |

(52) U.S. Cl.
CPC ............ *F01D 21/003* (2013.01); *F01D 25/24* (2013.01); *G01M 15/14* (2013.01); *G01N 21/8803* (2013.01); *G06T 7/0008* (2013.01); *F05D 2220/32* (2013.01); *G01N 2201/062* (2013.01); *G01N 2201/12* (2013.01); *G06T 2207/30164* (2013.01)

(58) Field of Classification Search
CPC ...... H04N 7/183; H04N 7/18; H04N 5/2252; G02B 23/2476; B25J 19/023
See application file for complete search history.

(56) References Cited

U.S. PATENT DOCUMENTS

| | | |
|---|---|---|
| 5,076,660 A | 12/1991 | Messinger |
| 5,741,965 A | 4/1998 | Hernandez et al. |
| 6,302,625 B1 | 10/2001 | Carey et al. |
| 6,919,956 B2 | 7/2005 | Kitagawa et al. |
| 7,016,035 B2 | 3/2006 | Wu et al. |

(Continued)

FOREIGN PATENT DOCUMENTS

| | | |
|---|---|---|
| EP | 1609957 A2 | 12/2005 |
| EP | 2267508 A2 | 12/2010 |

(Continued)

*Primary Examiner* — Sath V Perungavoor
*Assistant Examiner* — Howard D Brown, Jr.
(74) *Attorney, Agent, or Firm* — General Electric Company; Pamela A. Kachur

(57) ABSTRACT

A method for performing a visual inspection of a gas turbine engine may generally include inserting a plurality of optical probes through a plurality of access ports of the gas turbine engine. The access ports may be spaced apart axially along a longitudinal axis of the gas turbine engine such that the optical probes provide internal views of the gas turbine engine from a plurality of different axial locations along the gas turbine engine. The method may also include coupling the optical probes to a computing device, rotating the gas turbine engine about the longitudinal axis as the optical probes are used to simultaneously obtain images of an interior of the gas turbine engine at the different axial locations and receiving, with the computing device, image data associated with the images obtained by each of the optical probes at the different axial locations.

20 Claims, 6 Drawing Sheets

(56) References Cited

U.S. PATENT DOCUMENTS

| | | |
|---|---|---|
| 7,174,797 B2 | 2/2007 | Brostmeyer et al. |
| 7,271,894 B2 | 9/2007 | Devitt et al. |
| 7,379,077 B2 | 5/2008 | Bani-Hashemi et al. |
| 7,392,713 B2 | 7/2008 | Barkhoudarian |
| 7,449,658 B2 | 11/2008 | Mielke |
| 7,458,768 B2 | 12/2008 | Dube et al. |
| 8,181,528 B2 | 5/2012 | Reed et al. |
| 8,310,533 B2 | 11/2012 | Morse et al. |
| 8,563,080 B2 | 10/2013 | Hopkins |
| 8,713,999 B2 | 5/2014 | Hatcher |
| 8,714,038 B2 | 5/2014 | Moran et al. |
| 8,786,300 B2 | 7/2014 | Bendall |
| 8,812,154 B2 | 8/2014 | Vian et al. |
| 8,910,359 B2 | 12/2014 | Jones et al. |
| 2006/0088793 A1* | 4/2006 | Brummel ............. F23M 11/045 431/13 |
| 2010/0272557 A1* | 10/2010 | Woodmansee .......... F23N 5/082 415/118 |
| 2012/0026306 A1* | 2/2012 | Mitra ................. G01N 29/0654 348/61 |
| 2012/0203067 A1 | 8/2012 | Higgins et al. |
| 2013/0113915 A1 | 5/2013 | Scheid et al. |
| 2013/0192353 A1* | 8/2013 | Hatcher ............... F01D 21/003 73/112.01 |
| 2013/0194411 A1* | 8/2013 | Baleine ................. G02B 7/028 348/82 |
| 2013/0194412 A1* | 8/2013 | Hatcher ............... F01D 21/003 348/82 |
| 2013/0199040 A1 | 8/2013 | Dudeck et al. |
| 2014/0125791 A1* | 5/2014 | Arellano ............... G01N 21/47 348/82 |
| 2014/0309786 A1 | 10/2014 | Staehli et al. |
| 2015/0035968 A1* | 2/2015 | Konomura .......... G01N 21/954 348/82 |
| 2015/0036127 A1 | 2/2015 | Konomura et al. |
| 2015/0036130 A1* | 2/2015 | Konomura .......... G01M 15/02 356/241.6 |
| 2015/0054939 A1* | 2/2015 | DeAscanis .......... G01M 15/14 348/82 |
| 2015/0348253 A1* | 12/2015 | Bendall ................ G06T 7/0004 348/86 |
| 2016/0178532 A1* | 6/2016 | Lim ..................... G01N 21/954 348/46 |

FOREIGN PATENT DOCUMENTS

| | | |
|---|---|---|
| EP | 2711759 A1 | 3/2014 |
| WO | WO 2013/097944 A1 | 7/2013 |

* cited by examiner

SYSTEM AND METHOD FOR PERFORMING A VISUAL INSPECTION OF A GAS TURBINE ENGINE

CROSS-REFERENCE TO RELATED APPLICATIONS

This application claims priority to and is a continuation of U.S. patent application Ser. No. 14/963,665 filed on Dec. 9, 2015 and entitled "System and Method for Performing a Visual Inspection of a Gas Turbine Engine," the disclosure of which is hereby incorporated by reference herein in its entirety for all purposes.

FIELD OF THE INVENTION

The present subject matter relates generally to gas turbine engines and, more particularly, to a system and method for performing a visual inspection of a gas turbine engine.

BACKGROUND OF THE INVENTION

A gas turbine engine typically includes a turbomachinery core having a high pressure compressor, combustor, and high pressure turbine in serial flow relationship. The core is operable in a known manner to generate a primary gas flow. The high pressure compressor includes annular arrays ("rows") of stationary vanes that direct air entering the engine into downstream, rotating blades of the compressor. Collectively one row of compressor vanes and one row of compressor blades make up a "stage" of the compressor. Similarly, the high pressure turbine includes annular rows of stationary nozzle vanes that direct the gases exiting the combustor into downstream, rotating blades of the turbine. Collectively one row of nozzle vanes and one row of turbine blades make up a "stage" of the turbine. Typically, both the compressor and turbine include a plurality of successive stages.

In order to allow for periodic inspection of the core parts of the engine (e.g., the compressor blades and the turbine blades), borescope ports are typically provided in the engine casings and/or frames. Such ports allow optical borescope instruments to be inserted into the core engine to enable a visual inspection of the engine to be performed without requiring disassembly of the engine components. Currently, visual inspection methods require that an inspector insert a single borescope instrument into one of the borescope ports and visually inspect the portion of the engine viewable from such port as the engine is being manually rotated. As a result, a visual inspection of the entire engine using the borescope ports is generally a very time and labor intensive process. Moreover, if multiple inspectors are being used to inspect the engine, inspector-to-inspector variations typically exist with respect to the thoroughness and/or accuracy of the inspection.

Accordingly, an improved system and method for performing a visual inspection of a gas turbine engine would be welcomed within the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a method for performing a visual inspection of a gas turbine engine. The method may generally include inserting a plurality of optical probes through a plurality of access ports of the gas turbine engine. The access ports may be spaced apart axially along a longitudinal axis of the gas turbine engine such that the optical probes provide internal views of the gas turbine engine from a plurality of different axial locations along the gas turbine engine. The method may also include coupling the optical probes to a computing device, rotating the gas turbine engine about the longitudinal axis as the optical probes are used to simultaneously obtain images of an interior of the gas turbine engine at the different axial locations and receiving, with the computing device, image data associated with the images obtained by each of the optical probes at the different axial locations.

In another aspect, the present subject matter is directed to a system for performing a visual inspection of a gas turbine engine. The system may general include a plurality of access ports spaced apart axially along a longitudinal axis of the gas turbine engine and a plurality of optical probes installed through the plurality of access ports. The optical probes may be configured to provide internal views of the gas turbine engine from a plurality of different axial locations associated with the access ports. The system may also include a rotating device configured to rotate the gas turbine engine about the longitudinal axis as the optical probes are used to simultaneously obtain images of an interior of the gas turbine engine at the different axial locations. In addition, the system may include a computing device communicatively coupled to each of the optical probes. The computing device may be configured to receive image data associated with the images obtained by each of the optical probes at the different axial locations.

These and other features, aspects and advantages of the present invention will be better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
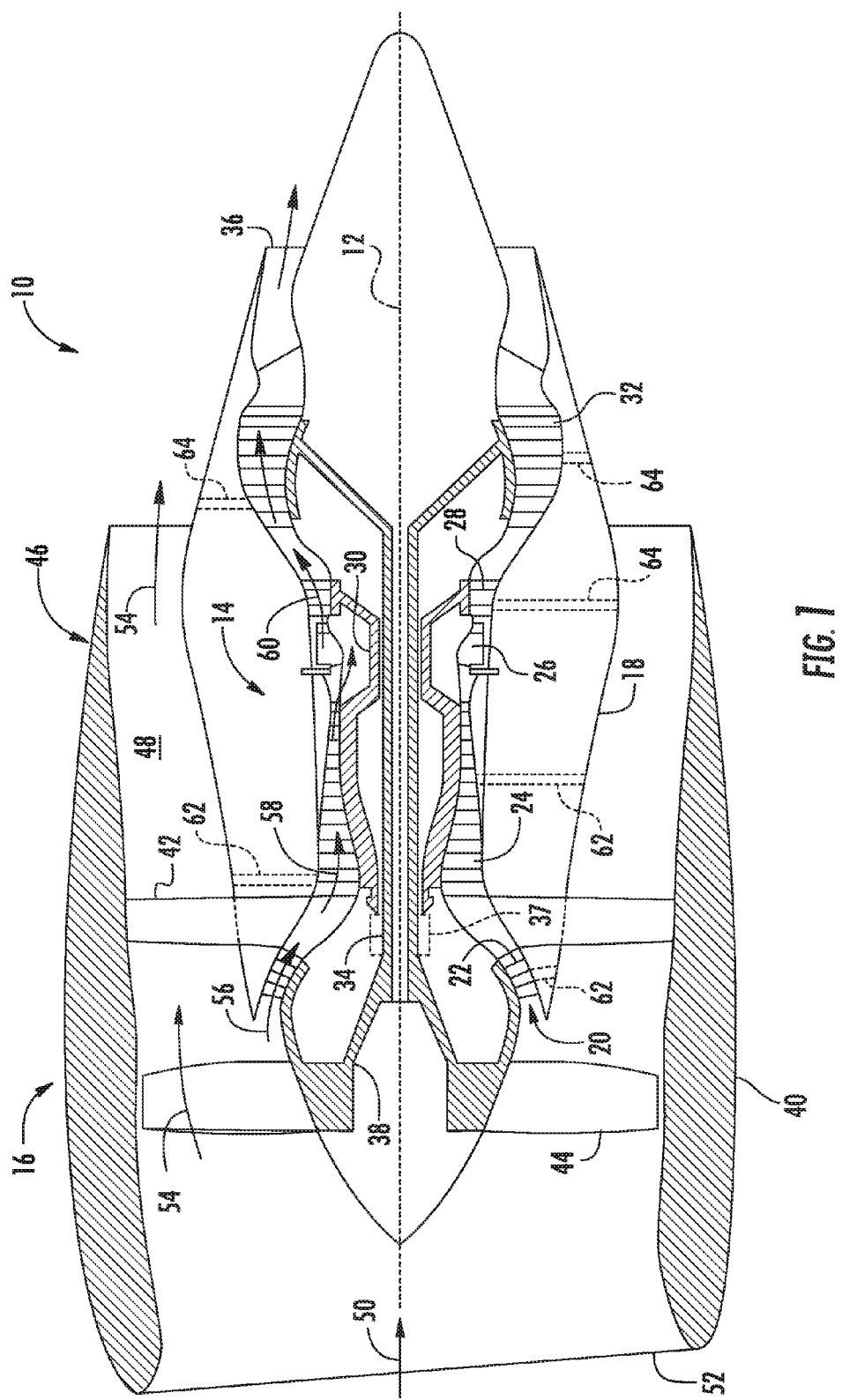
FIG. 1 illustrates a cross-sectional view of one embodiment of a gas turbine engine that may be utilized within an aircraft in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to an improved system and method for performing a visual inspection of a gas turbine engine. Specifically, in several embodiments, a plurality of optical probes (e.g., borescopes, fiberscopes, videoscopes and/or the like) may be inserted into a plurality of different access ports of the gas turbine engine, with each optical probe being communicatively coupled to a computing device. In addition, a rotating device (e.g., a motor) may also be communicatively coupled to the computing device for rotating the engine. In such an embodiment, to inspect the gas turbine engine, the computing device may be configured to control the operation of the rotating device such that the engine is rotated at a predefined or controlled speed. As the engine is being rotated, the computing device may collect image data associated with views or images of the interior of the engine obtained via the optical probes. As a result, image data may be collected for multiple sections of the engine (or for the entire engine) simultaneously, which may significantly improve the efficiency at which a visual inspection of the engine may be performed. For instance, in one embodiment, an optical probe may be inserted through the access port associated with each stage of a compressor and/or a turbine of the engine, thereby allowing the annular row of blades located within each compressor stage and/or turbine stage to be visually inspected simultaneously.

It should be appreciated that the disclosed system and method may generally be used to perform a visual inspection of any suitable type of gas turbine engine, including aircraft-based turbine engines and land-based turbine engines, regardless of the engine's current assembly state (e.g., fully or partially assembled). Additionally, with reference to aircraft engines, it should be appreciated that the present subject matter may be used on wing or off wing.

Referring now to the drawings, FIG. 1 illustrates a cross-sectional view of one embodiment of a gas turbine engine 10 that may be utilized within an aircraft in accordance with aspects of the present subject matter, with the engine 10 being shown having a longitudinal or axial centerline axis 12 extending therethrough for reference purposes. In general, the engine 10 may include a core gas turbine engine (indicated generally by reference character 14) and a fan section 16 positioned upstream thereof. The core engine 14 may generally include a substantially tubular outer casing 18 that defines an annular inlet 20. In addition, the outer casing 18 may further enclose and support a booster compressor 22 for increasing the pressure of the air that enters the core engine 14 to a first pressure level. A high pressure, multi-stage, axial-flow compressor 24 may then receive the pressurized air from the booster compressor 22 and further increase the pressure of such air. The pressurized air exiting the high-pressure compressor 24 may then flow to a combustor 26 within which fuel is injected into the flow of pressurized air, with the resulting mixture being combusted within the combustor 26. The high energy combustion products are directed from the combustor 26 along the hot gas path of the engine 10 to a first (high pressure) turbine 28 for driving the high pressure compressor 24 via a first (high pressure) drive shaft 30, and then to a second (low pressure) turbine 32 for driving the booster compressor 22 and fan section 16 via a second (low pressure) drive shaft 34 that is generally coaxial with first drive shaft 30. After driving each of turbines 28 and 32, the combustion products may be expelled from the core engine 14 via an exhaust nozzle 36 to provide propulsive jet thrust.

It should be appreciated that each compressor 22, 24 may include a plurality of compressor stages, with each stage including both an annular array of stationary compressor vanes and an annular array of rotating compressor blades positioned immediately downstream of the compressor vanes. Similarly, each turbine 28, 32 may include a plurality of turbine stages, with each stage including both an annular array of stationary nozzle vanes and an annular array of rotating turbine blades positioned immediately downstream of the nozzle vanes.

Additionally, as shown in FIG. 1, the fan section 16 of the engine 10 may generally include a rotatable, axial-flow fan rotor assembly 38 that is configured to be surrounded by an annular fan casing 40. It should be appreciated by those of ordinary skill in the art that the fan casing 40 may be configured to be supported relative to the core engine 14 by a plurality of substantially radially-extending, circumferentially-spaced outlet guide vanes 42. As such, the fan casing 40 may enclose the fan rotor assembly 38 and its corresponding fan rotor blades 44. Moreover, a downstream section 46 of the fan casing 40 may extend over an outer portion of the core engine 14 so as to define a secondary, or by-pass, airflow conduit 48 that provides additional propulsive jet thrust.

It should be appreciated that, in several embodiments, the second (low pressure) drive shaft 34 may be directly coupled to the fan rotor assembly 38 to provide a direct-drive configuration. Alternatively, the second drive shaft 34 may be coupled to the fan rotor assembly 38 via a speed reduction device 37 (e.g., a reduction gear or gearbox) to provide an indirect-drive or geared drive configuration. Such a speed reduction device(s) may also be provided between any other suitable shafts and/or spools within the engine 10 as desired or required.

During operation of the engine 10, it should be appreciated that an initial air flow (indicated by arrow 50) may enter the engine 10 through an associated inlet 52 of the fan casing 40. The air flow 50 then passes through the fan blades 44 and splits into a first compressed air flow (indicated by arrow 54) that moves through conduit 48 and a second compressed air flow (indicated by arrow 56) which enters the booster compressor 22. The pressure of the second compressed air flow 56 is then increased and enters the high pressure compressor 24 (as indicated by arrow 58). After mixing with fuel and being combusted within the combustor 26, the combustion products 60 exit the combustor 26 and flow through the first turbine 28. Thereafter, the combustion products 60 flow through the second turbine 32 and exit the exhaust nozzle 36 to provide thrust for the engine 10.

As indicated above, the gas turbine engine 10 may also include a plurality of access ports defined through its casings and/or frames for providing access to the interior of the core engine 14. For instance, as shown in FIG. 1, the engine 10 may include a plurality of access ports 62 (only three of which are shown) defined through the outer casing 18 for providing internal access to one or both of the compressors 22, 24. Similarly, as shown in the illustrated embodiment, the engine 10 may include a plurality of access ports 64 (only three of which are shown) defined through the outer casing 18 for providing internal access to one or both of the turbines 28, 32. In several embodiments, the access ports 62, 64 may be spaced apart axially along the core engine 14. For instance, the compressor access ports 62 may be spaced apart axially along each compressor 22, 24 such that at least one access port 62 is located at each compressor stage for providing access to the compressor vanes and blades located within such stage. Similarly, the turbine access ports 64 may be spaced apart axially along each turbine 28, 32 such that at least one access port 64 is located at each turbine stage for providing access to the nozzle vanes and turbine blades located within such stage.

It should be appreciated that, although the access ports 62, 64 are generally described herein with reference to providing internal access to one or both of the compressors 22, 24 and/or for providing internal access to one or both of the turbines 28, 32, the gas turbine engine 10 may include access ports providing access to any suitable internal location of the engine 10, such as by including access ports that provide access within the combustor 26 and/or any other suitable component of the engine 10.

Figure 2:
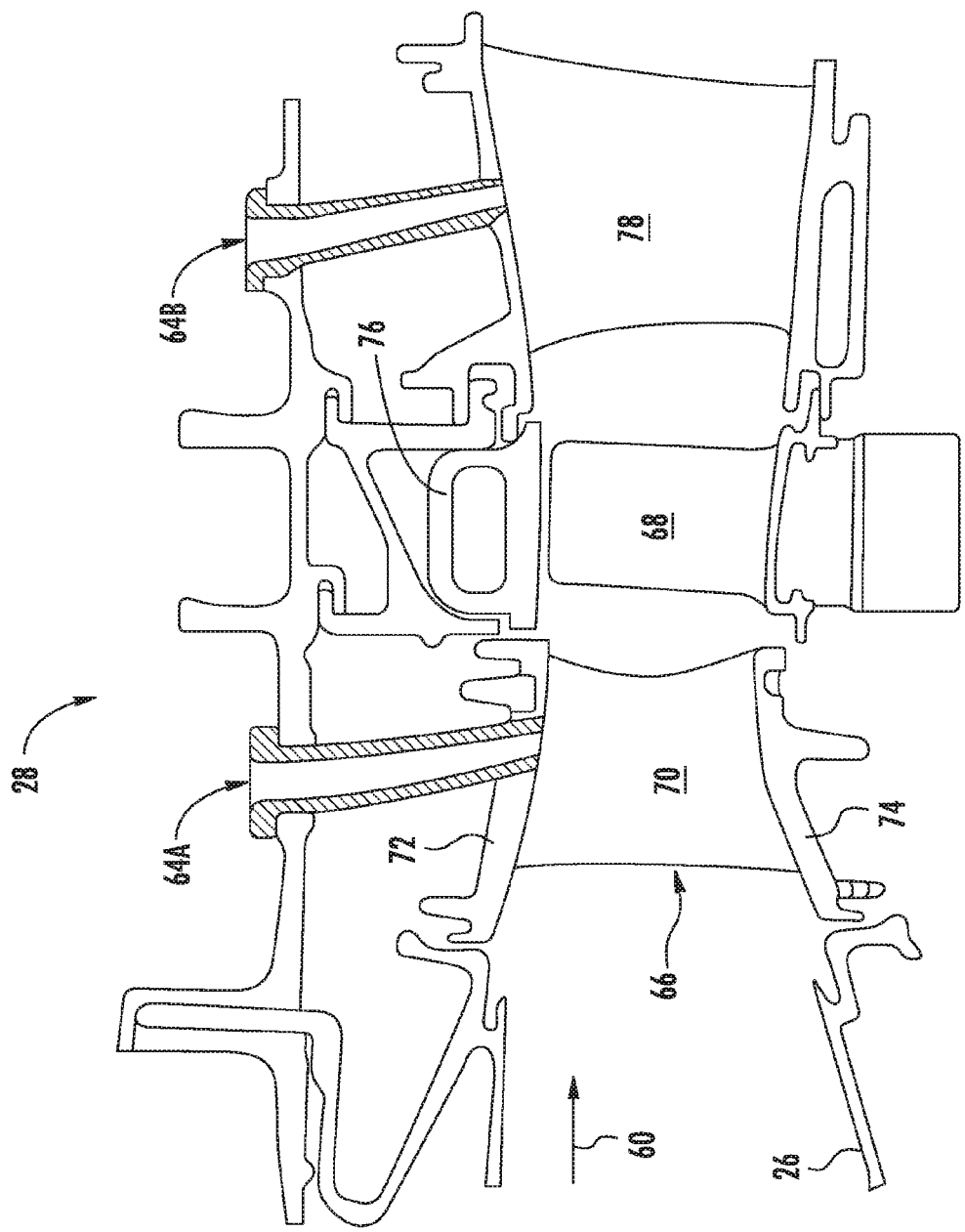
FIG. 2 illustrates a partial, cross-sectional view of one embodiment of a turbine suitable for use within the gas turbine engine shown in FIG. 1, particularly illustrating access ports defined in the engine for providing internal access to the turbine.

Referring now to FIG. 2, a partial, cross-sectional view of the first (or high pressure) turbine 28 described above with reference to FIG. 1 is illustrated in accordance with embodiments of the present subject matter. As shown, the first turbine 28 may include a first stage turbine nozzle 66 and an annular array of rotating turbine blades 68 (one of which is shown) located immediately downstream of the nozzle 66. The nozzle 66 may generally be defined by an annular flow channel that includes a plurality of radially-extending, circularly-spaced nozzle vanes 70 (one of which is shown). The vanes 70 may be supported between a number of arcuate outer bands 72 and arcuate inner bands 74. Additionally, the circumferentially spaced turbine blades 68 may generally be configured to extend radially outwardly from a rotor disk (not shown) that rotates about the centerline axis 12 (FIG. 1) of the engine 10. Moreover, a turbine shroud 76 may be positioned immediately adjacent to the radially outer tips of the turbine blades 68 so as to define the outer radial flowpath boundary for the combustion products 60 flowing through the turbine 28 along the hot gas path of the engine 10.

As indicated above, the turbine 28 may generally include any number of turbine stages, with each stage including an annular array of nozzle vanes and follow-up turbine blades 68. For example, as shown in FIG. 2, an annular array of nozzle vanes 78 of a second stage of the turbine 28 may be located immediately downstream of the turbine blades 68 of the first stage of the turbine 28.

Moreover, as shown in FIG. 2, a plurality of access ports 64 may be defined through the turbine casing and/or frame, with each access port 64 being configured to provide access to the interior of the turbine 28 at a different axial location. Specifically, as indicated above, the access ports 64 may, in several embodiments, be spaced apart axially such that each access port 64 is aligned with or otherwise provides interior access to a different stage of the turbine 28. For instance, as shown in FIG. 2, a first access port 64A may be defined through the turbine casing/frame to provide access to the first stage of the turbine 28 while a second access port 64B may be defined through the turbine casing/frame to provide access to the second stage of the turbine 28.

It should be appreciated that similar access ports 64 may also be provided for any other stages of the turbine 28 and/or for any turbine stages of the second (or low pressure) turbine 32. It should also be appreciated that, in addition to the axially spaced access ports 64 shown in FIG. 2, access ports may be also provided at differing circumferentially spaced locations. For instance, in one embodiment, a plurality of circumferentially spaced access ports may be defined through the turbine casing/frame at each turbine stage to provide interior access to the turbine 28 at multiple circumferential locations around the turbine stage.

Figure 3:
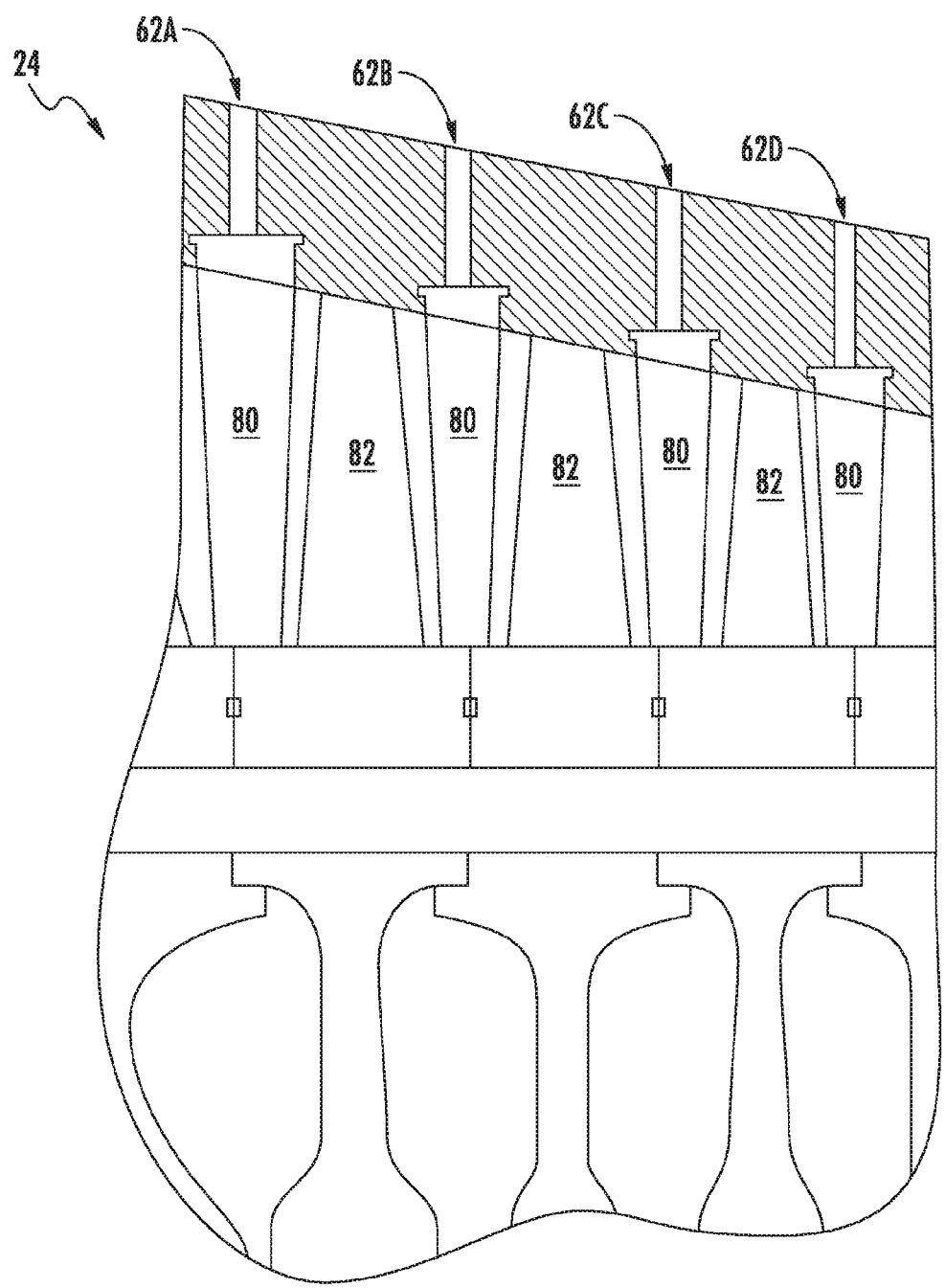
FIG. 3 illustrates a partial, cross-sectional view of one embodiment of a compressor suitable for use within the gas turbine engine shown in FIG. 1, particularly illustrating access ports defined in the engine for providing internal access to the compressor.

Referring now to FIG. 3, a partial, cross-sectional view of the high pressure compressor 24 described above with reference to FIG. 1 is illustrated in accordance with embodiments of the present subject matter. As shown, the compressor 24 may include a plurality of compressor stages, with each stage including both an annular array of fixed compressor vanes 80 (only one of which is shown for each stage) and an annular array of rotatable compressor blades 82 (only one of which is shown for each stage). Each row of compressor vanes 80 is generally configured to direct air flowing through the compressor 24 to the row of compressor blades 82 immediately downstream thereof.

Moreover, as indicated above, the compressor 24 may include a plurality of access ports 62 defined through the compressor casing/frame, with each access port 62 being configured to provide access to the interior of the compressor 24 at a different axial location. Specifically, in several embodiments, the access ports 62 may be spaced apart axially such that each access port 62 is aligned with or otherwise provides interior access to a different stage of the compressor 24. For instance, as shown in FIG. 3, first, second, third and fourth access ports 62A, 62B, 62C, 62D are illustrated that provide access to four successive stages, respectively, of the compressor 24.

It should be appreciated that similar access ports may also be provided for any of the other stages of the compressor 24 and/or for any of the stages of the low pressure compressor 22. It should also be appreciated that, in addition to the axially spaced access ports 62 shown in FIG. 3, access ports may be also provided at differing circumferentially spaced locations. For instance, in one embodiment, a plurality of circumferentially spaced access ports may be defined through the compressor casing/frame at each compressor stage to provide interior access to the compressor 24 at multiple circumferential locations around the compressor stage.

Figure 4:
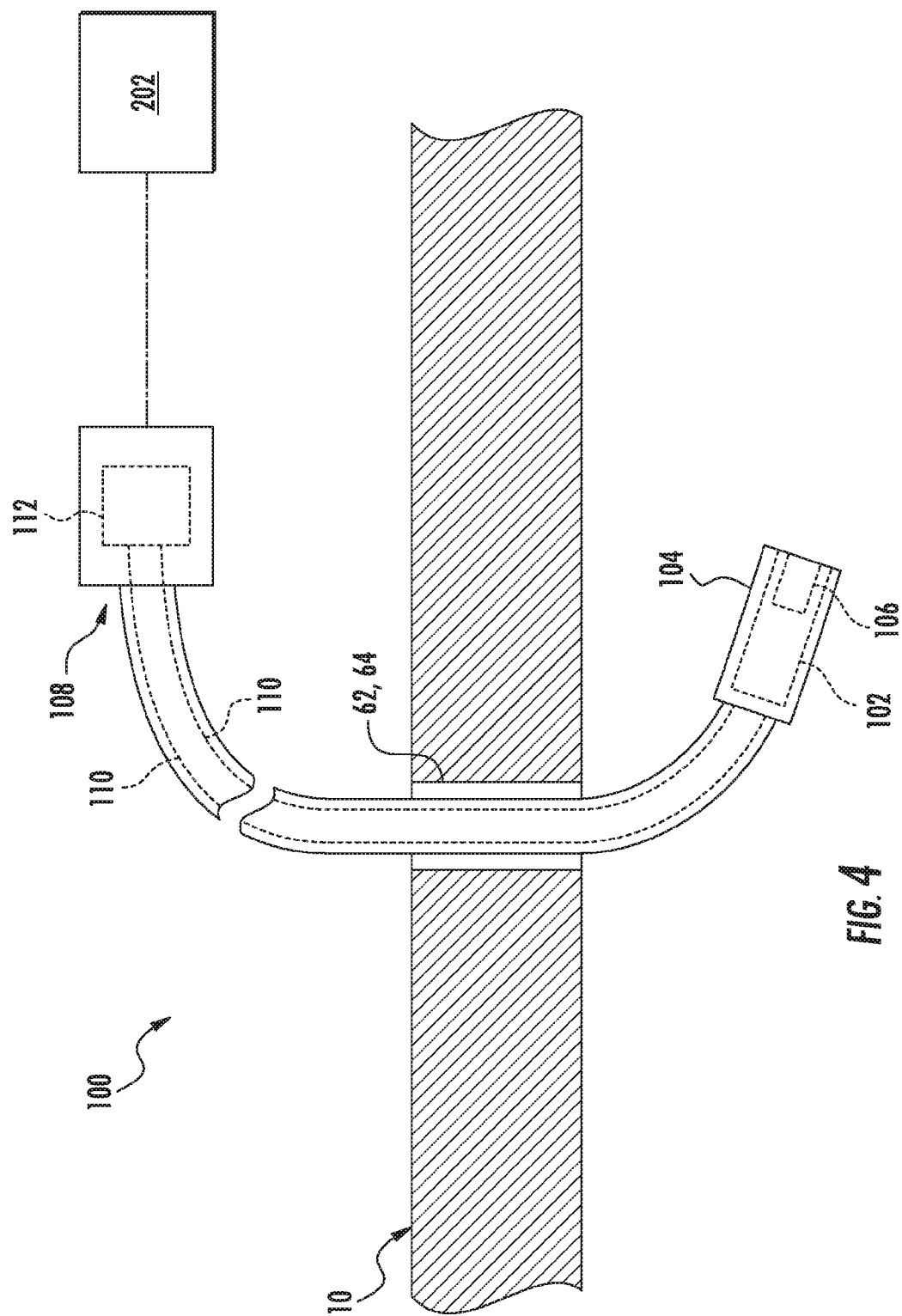
FIG. 4 illustrates a simplified view of one embodiment of an optical probe that may be used in accordance with aspects of the present subject matter to visually inspect a gas turbine engine.

Referring now to FIG. 4, a simplified view of one embodiment of an optical probe 100 that may be utilized to perform a visual inspection of a gas turbine engine 10 is illustrated in accordance with aspects of the present subject matter. As shown, the optical probe 100 has been inserted through an access port of the engine 10, such as one of the turbine access ports 64 described above with reference to FIG. 2 or one of the compressor access ports 62 described above with reference to FIG. 3.

In general, the optical probe 100 may correspond to any suitable optical device that may be inserted through an access port 62, 64 of the gas turbine engine 10 to allow images of the interior of the engine 10 to be captured or otherwise obtained. For instance, in several embodiments, the optical probe 100 may correspond to a borescope, videoscope, fiberscope or any other similar optical device known in the art that allows for the interior of a gas turbine engine 10 to be viewed through an access port 62, 64. In such embodiments, the optical probe 100 may include one or more optical elements (indicated schematically by dashed box 102), such as one or more optical lenses, optical fibers, image capture devices, cables, and/or the like, for obtaining views or images of the interior of the engine 10 at a tip 104 of the probe 100 and for transmitting or relaying such images from the probe tip 104 along the length of the probe 100 to the exterior of the engine 10. For instance, as shown in FIG. 4, the interior views or images obtained by the probe 100 may be transmitted from the probe tip 104 to a computing device 202 connected or otherwise coupled to the probe 100. Additionally, as shown in FIG. 4, in one embodiment, a light source (indicated by dashed box 106), such as an LED, may be provided at or adjacent to the probe tip 104 to provide lighting within the interior of the engine 10.

The optical probe 100 may also include an articulation assembly 108 that allows the orientation of the probe tip 104 to be adjusted within the interior of the gas turbine engine 10. For example, the articulation assembly 108 may allow for the probe tip 104 to be rotated or pivoted about a single axis or multiples axes to adjust the orientation of the tip 104 relative to the remainder of the probe 100. It should be appreciated that the articulation assembly 108 may generally have any suitable configuration and/or may include any suitable components that allow for adjustment of the orientation of the probe tip 104 relative to the remainder of the probe 100. For example, in one embodiment, a plurality of articulation cables 110 may be coupled between the probe tip 104 and one or more articulation motors 112. In such an embodiment, by adjusting the tension of the cables 110 via the motor(s) 112, the probe tip 104 may be reoriented within the gas turbine engine 10.

It should also be appreciated that, in several embodiments, the articulation assembly 108 may be configured to be electronically controlled. Specifically, as shown in FIG. 4, the computing device 202 may be communicatively coupled to the articulation assembly 108 to allow the computing device 202 to adjust the orientation of the probe tip 104 via control of the articulation assembly 108. For instance, in the illustrated embodiment, the computing device 202 may be configured to transmit suitable control signals to the articulation motor(s) 112 in order to adjust the tension within the associated cable(s) 110, thereby allowing the computing device 202 to automatically adjust the orientation of the probe tip 104 within the gas turbine engine 10.

It should also be appreciated that, although not shown, the optical probe 100 may also include a location signal receiver positioned at or adjacent to its probe tip 104. In such an embodiment, the location signal receiver may be configured to receive location-related signals from a plurality of location transmitters mounted on or within the engine 10 that provide an indication of the position of the location signal receiver (and, thus, the probe tip 104) relative to the location transmitters. For instance, the location signal receiver may be configured to receive signals from the location transmitters that provide an indication of the distance defined between the receiver and each transmitter (e.g., based on the signal strength, the time of flight of the signals and/or time of arrival of the signals) and/or that provide an indication of the angle defined between the receiver and each transmitter (e.g., based on the angle of incidence or angle of arrival of the signals). The signals received by the location signal receiver may then be transmitted to the computing device 202 to allow the computing device 202 to determine the current location of the probe tip 104 within the gas turbine engine 10 using any suitable signal-based positioning technique, such as a trilateration technique or a triangulation technique.

Figure 5:
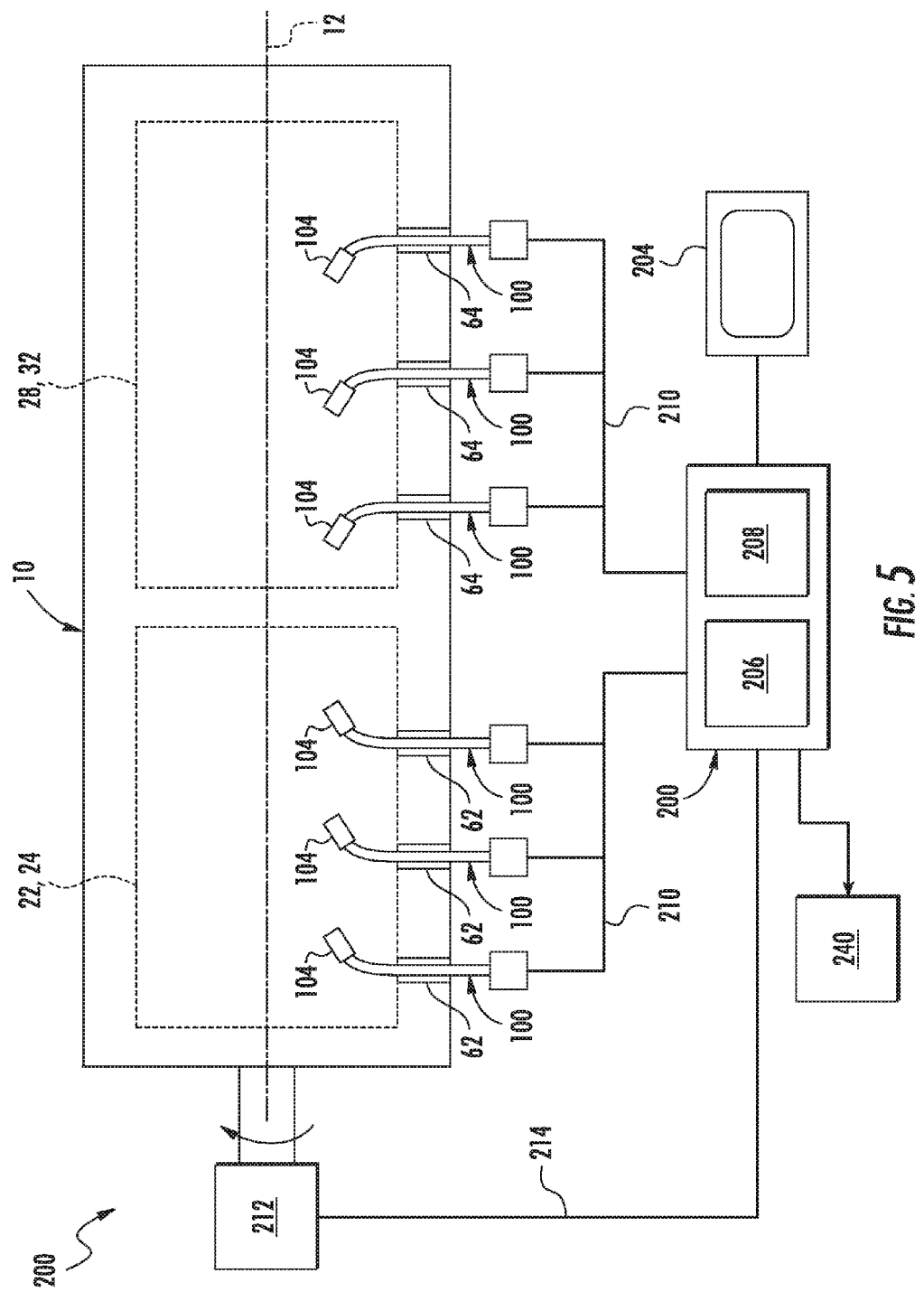
FIG. 5 illustrates a simplified, schematic view of one embodiment of a system for performing a visual inspection of a gas turbine engine in accordance with aspects of the present subject matter.

Referring now to FIG. 5, a simplified, schematic view of one embodiment of a system 200 for visually inspecting a gas turbine engine is illustrated in accordance with aspects of the present subject matter. As shown, the system 200 may generally include a computing device 202 and a plurality of optical probes 100 installed within corresponding access ports 62, 64 of the gas turbine engine 10. The optical probes 100 may generally be configured to provide internal views of the gas turbine engine 10 from a plurality of different axial perspectives within the engine 10. The internal images obtained via the optical probes 100 may then be transmitted to the computing device 202 as image data for subsequent storage thereon and/or for presentation to a user of the system 200 via a display device 204 associated with the computing device.

In general, the computing device 202 may correspond to any suitable processor-based device and/or any suitable combination of processor-based devices. Thus, in several embodiments, the computing device 202 may include one or more processor(s) 206 and associated memory device(s) 208 configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 208 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 208 may generally be configured to store suitable computer-readable instructions that, when implemented by the processor(s) 206, configure the computing device 202 to perform various functions including, but not limited to, receiving, processing and/or storing the image data transmitted from the optical probes 100.

As shown in FIG. 5, the computing device 202 may be communicatively coupled to each of the optical probes 100 (e.g., via communicative links or cables 210). As such, image data associated with the views or images obtained by each of the optical probes 100 may be transmitted to the computing device 202. Such image data may then be used to allow the interior of the gas turbine engine 10 to be visually inspected at or adjacent to the various axial locations of the access ports 62, 64. For example, in one embodiment, the image data may be stored within the device's memory 208 to allow the images to be analyzed at a later time/date to identify defects and/or damage within the engine 10. In addition (or an alternative thereto), the image data may be transmitted from the computing device 202 to the associated display device 204 to allow a user of the system 200 to view the various internal images provided by the optical probes 100.

It should be appreciated that, in one embodiment, each probe 100 may be configured to continuously capture images of the interior of the gas turbine engine 10. Alternatively, each probe 100 may be configured to only capture a single image or multiple images that may be stitched together to generate a three-dimensional model of the internal component(s) being inspected.

Moreover, as shown in FIG. 5, in several embodiments, the system 200 may include a rotating device 212 configured to rotate the gas turbine engine 10 about its longitudinal axis 12. For example, in one embodiment, the rotating device 212 may correspond to a motor rotatably coupled to a drive shaft of the engine 10 (e.g., drive shaft 30 or drive shaft 34 shown in FIG. 1), either directly or indirectly via a gearbox or other rotational coupling. As such, by rotating the engine 10 via the motor, the various rotating components of the engine 10 may be rotated about the engine's axis 12, thereby allowing an entire annular array of rotating components to be inspected using a single optical probe 100 positioned within a single access port 62, 64. For example, using an optical probe 100 inserted through an access port 62 configured to provide access to a given stage of a compressor 22, 24 of the gas turbine engine 10, images of the entire annular array of compressor blades 82 located within such stage may be obtained using the optical probe 100 as the engine 10 is being rotated. Similarly, using an optical probe 100 inserted through an access port 64 providing access to a given stage of a turbine 28, 32 of the gas turbine engine 10, images of the entire annular array of turbine blades 68 located within such stage may be obtained using the optical probe 100 as the engine 10 is being rotated.

In several embodiments, the computing device 202 may be configured to electronically control the operation of the rotating device 212. For example, as shown in FIG. 5, the computing device 202 may be communicatively coupled to the rotating device 212 via a communicative link or cable 214. As such, the computing device 202 may be configured to transmit control signals to the rotating device 212 for controlling its operation. For instance, the computing device 202 may be configured to start/stop the rotating device 212 and/or control the operation of the rotating device 212 such that the engine 10 is rotated at a pre-determined or pre-defined speed as the optical probes 100 are being used to obtain images of the interior of the engine 10.

It should be appreciated that, by inserting multiple optical probes 100 into various different access ports 62, 64 of the engine 10 and by coupling such probes 100 to the computing device 202, a plurality of different axial sections of the engine 10 may be visually inspected at the same time. For example, as indicated above, the gas turbine engine 10 may include a plurality of access ports 62 spaced apart axially along at least a portion of a compressor 22, 24 of the engine 10, with each access port 62 providing access to a different compressor stage of the compressor 24, 24. Thus, by inserting optical probes 100 into each of the compressor access ports 62 and by rotating the engine 10, images of the circumferential arrays of compressor blades 82 contained within the various compressor stages may be obtained simultaneously. The images may then be inspected to determine if any of the compressor blades 82 have been damaged or contain defects.

Similarly, as indicated above, the gas turbine engine 10 may include a plurality of access ports 64 spaced apart axially along at least a portion of a turbine 28, 32 of the engine 10, with each access port 64 providing access to a different turbine stage of the turbine 28, 32. Thus, by inserting optical probes 100 into each of the turbine access ports 64 and by rotating the engine 10, images of the circumferential arrays of turbine blades 68 contained within the various turbine stages may be obtained simultaneously. The images may then be inspected to determine if any of the turbine blades 68 have been damaged or contain defects.

It should be appreciated that, in one embodiment, the computing device 202 may be configured to automatically inspect the internal component(s) depicted in the images obtained via the probes 100 for any defects and/or damage. For instance, the computing device 202 may be configured to implement a computer-vision technique or any other suitable image-processing technique to automatically detect any defects/damage associated with one or more of the internal components of the engine 10. In such an embodiment, the computing device 202 may be configured to compare the results of the visual inspection to any applicable manuals associated with the engine 10 (e.g., an engine maintenance manual and/or an aircraft maintenance manual). Thereafter, the computing device 202 may present the inspection results in real-time to a user of the system 200 (e.g., via the display device 204), including presenting the comparison of the results to the applicable engine-related manual(s) to allow the user to determine if any follow-up repair procedures and/or other procedures may need to be performed.

It should also be appreciated that, for purposes of illustration, the schematic view of the engine 10 shown in FIG. 5 simples includes three compressor access ports 62 and three turbine access ports 64, with corresponding optical probes 100 being installed within each port 62, 64. However, as indicated above, the gas turbine engine 10 may generally include any number of access ports (including any number of compressor access ports 62 and turbine access ports 64) for providing access to the interior of the engine 10. As such, it should be readily appreciated that, for a given number of access ports defined within a gas turbine engine 10, a corresponding number of optical probes 100 may similarly be inserted through such ports and coupled to the computing device 202 to allow various different locations within the gas turbine engine 10 to be visually inspected simultaneously. For instance, by inserting an optical probe 100 into every access port defined within a gas turbine engine 10, the disclosed system 200 may be used to simultaneously collect images of the entire engine 10.

Moreover, as indicated above, each optical probe 100 may include an articulation assembly 108 that allows for the orientation of the probe tip 104 to be adjusted within the engine 10. In such an embodiment, the computing device 202 may be configured to control the operation of the articulation assemblies 108, either individually or collectively, to allow the orientation of the probe tips 104 to be adjusted. Such automatic control of the tip orientation may provide a means for a user of the system 200 to manipulate the perspective of the internal view(s) provided by a given probe(s) as the images obtained by such probe(s) are being presented to the user.

Further, as shown in FIG. 5, the computing device 202 may, in one embodiment, be configured to transmit any inspection-related data acquired by the computing device 202 (e.g., image data, inspection results, etc.) to a centralized data center 240 for subsequent storage and/or processing of the data. For example, the centralized data center 240 may correspond to a remote server(s) or computing device(s) that is configured to communicate with the local computing device 202 via any suitable network, such as any suitable wired or wireless network(s) (e.g., a wide-area network (WAN)) that allows the computing device 202 and the data center 240 to communicate with one another via any suitable communications protocol (e.g. TCP/IP, HTTP, SMTP, FTP) and/or using any suitable encodings/formats (e.g. HTML, JSON XML) and/or protection schemes (e.g. VPN, secure HTTP, SSL). As a result, inspection-related data acquired using the disclosed system 200 may be transmitted from a plurality of different inspection sites or locations to a single centralized location.

Figure 6:
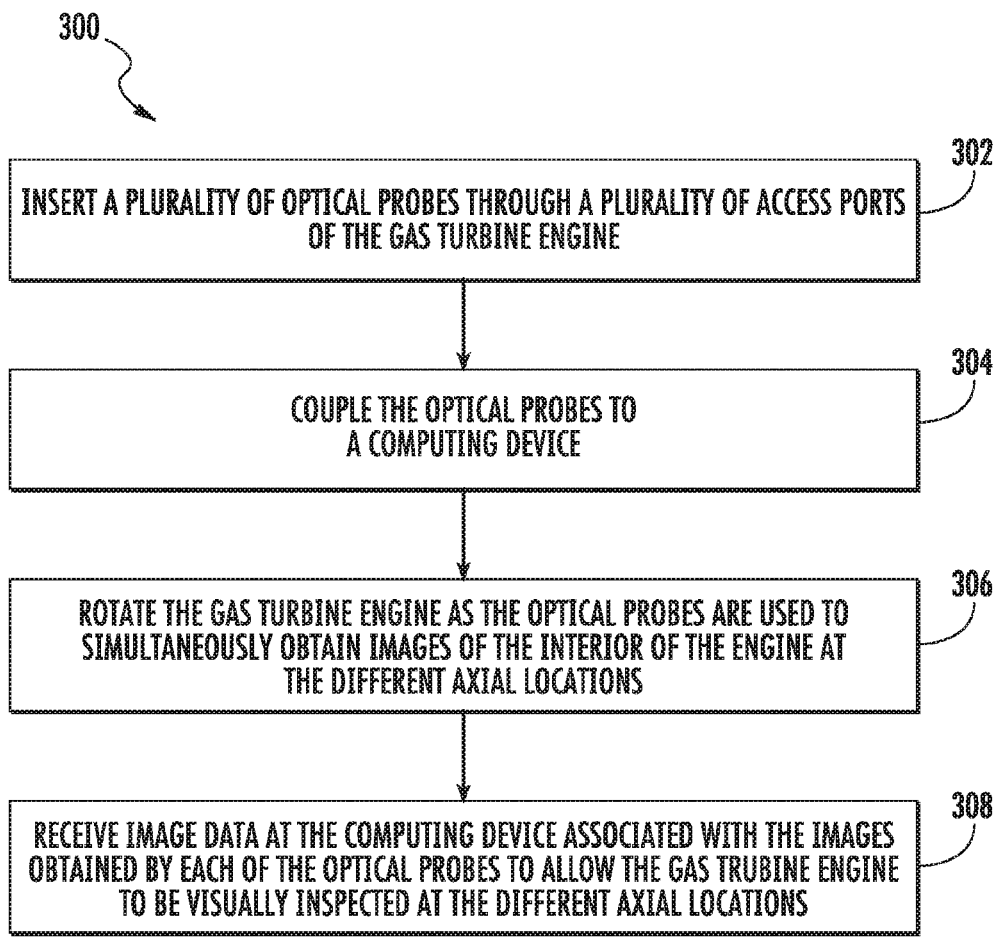
FIG. 6 illustrates a flow diagram of one embodiment of a method for performing a visual inspection of a gas turbine engine in accordance with aspects of the present subject matter.

Referring now to FIG. 6, a flow diagram of one embodiment of a method 300 for performing a visual inspection of a gas turbine engine is illustrated in accordance with aspects of the present subject matter. In general, the method 300 will be discussed herein with reference to the gas turbine engine 10 and the system 200 described above with reference to FIGS. 1-5. However, it should be appreciated by those of ordinary skill in the art that the disclosed method 300 may generally be implemented with gas turbine engines having any other suitable engine configuration and/or with systems having any other suitable system configuration. In addition, although FIG. 6 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 6, at (302), the method 300 may include inserting a plurality of optical probes through a plurality of access ports of the gas turbine engine. Specifically, as indicated above, optical probes 100 may be inserted into any number of the access ports defined within the gas turbine engine 10, such as any of the compressor access ports 62 and/or any of the turbine access ports 64. Additionally, at (304), the method 300 may include coupling the optical probes to a computing device. For example, as described above, each optical probe 100 may be communicatively coupled to a computing device 202, which may allow the internal views or images obtained by the probes 100 to be transmitted to the computing device 202.

Moreover, as shown in FIG. 6, at (306), the method 300 may include rotating the gas turbine engine as the optical probes are used to simultaneously obtain images of the interior of the engine at the various different axial locations. For example, as indicated above, a rotating device 212 may be coupled to the engine 10 to allow the engine 10 to be rotated about its longitudinal axis 12 as the probes 100 are being used to obtain images of the interior of the engine 10. Additionally, as indicated above, the rotating device 212 may, in several embodiments, be communicatively coupled to the computing device 202 of the disclosed system 200. As such, the computing device 202 may be configured to automatically control the operation of the rotating device 212 to allow the engine 10 to be rotated at a controlled speed.

Referring still to FIG. 6, at (308), the method 300 may include receiving image data at the computing device associated with the images obtained by each of the optical probes to allow the gas turbine engine to be visually inspected at the different axial locations. For example, as indicated above, the computing device 202 may be configured to collect image data associated with the views or images provided by the optical probes 100. Such image data may then be stored within the device's memory 208 and/or presented to a user of the system 200 via an associated display device 204.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for performing a visual inspection of a gas turbine engine, the method comprising:
   inserting a plurality of optical probes through a plurality of access ports of the gas turbine engine, the plurality of access ports being spaced apart axially along a longitudinal axis of the gas turbine engine such that the plurality of optical probes provide internal views of the gas turbine engine from a plurality of different axial locations along the gas turbine engine;
   coupling the plurality of optical probes to a computing device;
   rotating the gas turbine engine about the longitudinal axis as the plurality of optical probes are used to simultaneously obtain images of an interior of the gas turbine engine at the plurality of different axial locations; and
   receiving, with the computing device, image data associated with the images obtained by each of the plurality of optical probes at the plurality of different axial locations.

2. The method of claim 1, wherein the plurality of access ports are spaced apart axially along at least a portion of a compressor of the gas turbine engine such that each access port is located at or adjacent to a different stage of a plurality of stages of the compressor.

3. The method of claim 2, wherein rotating the gas turbine engine comprises rotating the gas turbine engine about the longitudinal axis as the plurality of optical probes are used to obtain images of a plurality of compressor blades located at each of the plurality of stages of the compressor.

4. The method of claim 3, further comprising inspecting the plurality of compressor blades for defects or damage based on the image data associated with the obtained images.

5. The method of claim 1, wherein the plurality of access ports are spaced apart axially along at least a portion of a turbine of the gas turbine engine such that each access port is located at or adjacent to a different stage of a plurality of stages of the turbine.

6. The method of claim 5, wherein rotating the gas turbine engine comprises rotating the gas turbine engine about the longitudinal axis as the plurality of optical probes are used to obtain images of a plurality of turbine blades located at each of the plurality of stages of the turbine.

7. The method of claim 6, further comprising inspecting the plurality of turbine blades for defects or damage based on the image data associated with the obtained images.

8. The method of claim 1, wherein an orientation of a probe tip of each of the plurality of optical probes is adjustable within the gas turbine engine, further comprising adjusting, with the computing device, the orientation of at least one of the probe tips as images of the interior of the gas turbine engine are being obtained.

9. The method of claim 1, further comprising providing for display, by the computing device, the image data on a display device.

10. The method of claim 1, further comprising storing the image data within a memory associated with the computing device.

11. The method of claim 1, wherein rotating the gas turbine engine comprises transmitting, by the computing device, control signals to a motor rotatably coupled to the gas turbine engine such that the motor rotates the gas turbine engine at a controlled speed about the longitudinal axis.

12. The method of claim 1, wherein each of the plurality of optical probes corresponds to one of a borescope, a videoscope or a fiberscope.

13. The method of claim 1, wherein each of the plurality of optical probes includes a light source for illuminating the interior of the gas turbine engine.

14. A method for performing a visual inspection of a gas turbine engine, the method comprising:

inserting a plurality of optical probes through a plurality of access ports of the gas turbine engine, the plurality of access ports being spaced apart axially along a longitudinal axis of the gas turbine engine such that the plurality of optical probes provide internal views of the gas turbine engine from a plurality of different axial locations along the gas turbine engine;

coupling the plurality of optical probes to a computing device;

transmitting, by the computing device, control signals to a motor rotatably coupled to the gas turbine engine such that the motor rotates the gas turbine engine at a controlled speed about the longitudinal axis as the plurality of optical probes are used to simultaneously obtain images of an interior of the gas turbine engine at the plurality of different axial locations;

receiving, with the computing device, image data associated with the images obtained by each of the plurality of optical probes at the plurality of different axial locations; and transmitting, with the computing device, the image data to a data center located remote to the computing device.

15. The method of claim 14, wherein the plurality of access ports are spaced apart axially along at least a portion of a compressor of the gas turbine engine such that each access port is located at or adjacent to a different stage of a plurality of stages of the compressor.

16. The method of claim 15, wherein rotating the gas turbine engine comprises rotating the gas turbine engine about the longitudinal axis as the plurality of optical probes are used to obtain images of a plurality of compressor blades located at each of the plurality of stages of the compressor.

17. The method of claim 16, further comprising inspecting the plurality of compressor blades for defects or damage based on the image data associated with the obtained images.

18. The method of claim 14, wherein the plurality of access ports are spaced apart axially along at least a portion of a turbine of the gas turbine engine such that each access port is located at or adjacent to a different stage of a plurality of stages of the turbine.

19. The method of claim 18, wherein rotating the gas turbine engine comprises rotating the gas turbine engine about the longitudinal axis as the plurality of optical probes are used to obtain images of a plurality of turbine blades located at each of the plurality of stages of the turbine.

20. The method of claim 19, further comprising inspecting the plurality of turbine blades for defects or damage based on the image data associated with the obtained images.

* * * * *

UNITED STATES PATENT AND TRADEMARK OFFICE
CERTIFICATE OF CORRECTION

| | | |
|---|---|---|
| PATENT NO. | : 9,458,735 B1 | Page 1 of 1 |
| APPLICATION NO. | : 15/040310 | |
| DATED | : October 4, 2016 | |
| INVENTOR(S) | : Diwinsky et al. | |

It is certified that error appears in the above-identified patent and that said Letters Patent is hereby corrected as shown below:

In the Specification

In Column 11, Line 4, delete "JSON XML)" and insert -- JSON, XML) --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*